United States Patent [19]
Cole et al.

[11] Patent Number: 6,037,129
[45] Date of Patent: Mar. 14, 2000

[54] MULTI-MARKER RT-PCR PANEL FOR DETECTING METASTATIC BREAST CANCER

[75] Inventors: David J. Cole, Mt. Pleasant; Paul L. Baron; Paul H. O'Brien, both of Charleston, all of S.C.

[73] Assignee: Medical University of South Carolina, S.C.

[21] Appl. No.: 09/086,372

[22] Filed: May 28, 1998

[51] Int. Cl.$^7$ .............................. C12Q 1/68; C07H 21/04
[52] U.S. Cl. ............................................. 435/6; 536/24.3
[58] Field of Search ........................................ 435/6, 91.2

[56] References Cited

PUBLICATIONS

Lockett et al. "Detection of Occult Breast Cancer Micrometastases in Axillary Lymph Nodes Using a Multimarker Reverse Transcriptase–Polymerase Chain Reaction Panel" *J. Am. Coll. Surg.* 187:9–16, 1998.

Lockett et al. "Efficacy of Reverse Transcriptase–Polymerase Chain Reaction Screening for Micrometastic Disease in Axillary Lymph Nodes of Breast Cancer Patients" *Amer. Surg.* 64:539–544, Jun. 1998.

Lockett et al. "Occult Breast Cancer Micrometastases: Detection in Axillary Lymph Nodes using a Multimarker Reverse . . . " Reprinterd from Surgical Forum, vol. XLVIII, pp. 861–863, 1997.

Noguchi S, Aihara R, Motamura K, et al. "Histologic Characteristics of Breast Cancers with Occult Lymph Node Metastases Detected by Keratin 19 mRNA Reverse Transcriptase–Polymerase Chain Reaction" *Cancer* 78:1235–1240, 1996.

Hahnel and Hahnel "Expression of the PIP/GCDFP–15 Gene and Survival in Breast Cancer" Virchows Archives—An International Journal of Pathology, 429(6):365–369, Dec. 1996.

Autiero et al. "A 17 kDa CD4–Binding Glycoprotein Present in Human Seminal Plasma and In Breast–Tumor Cells" *Europ. J. Immunol.* 25(5):1461–1464, May 1995.

Pagani et al. "PIP/GCDFP–15 Gene–Expression and Apocrine Differentiation in Carcinomas of the Breast" Virchows Archives—An International Journal of Pathology, 425(5):459–465, Dec. 1994.

Hahnel et al. "Hormone–Regulated Genes (pS2, PIP, FAS) in Breast–Cancer and Nontumoral Mammary Tissue" *Pathobiol.* 62(2);82–89, Mar.–Apr. 1994.

Bonneterre et al. "Biological and Clinical Aspects of Prolactin Receptors (PRL–R) in Human Breast Cancer" *J. Steroid Biochem. Mol. Biol.* 37(6):977–981, 1990.

Murphy et al. "Expression of the Gene Encoding a Prolactin–Incucible Protein by Human Breast Cancers In Vivo Correlation with Steroid Receptor Status" *Cancer Res.* 47(5):4160–4164, Aug. 1987.

Shiu R and Iwasiow B. "Prolactin–Inducible proteins in human breast cancer cells" *J Biol Chem* 260(20):11307–11313, Sep. 15, 1985.

Colby W, Chen E, Smith D, and Levinson A. "Identification and Nucleotide Sequence of a Human Locus Homologus to the v–myc Oncogene of Avian Myelocytomatosis Virus MC29" *Nature* 301:722–725, 1983.

Yun et al. "Keratin 19 mRNA is detectable by RT–PCr in lymph nodes of patients without breast cancer", British Journal of Cancer, vol. 76, pp. 1112–1113, 1997.

*Primary Examiner*—Lisa B. Arthur
*Assistant Examiner*—Jehanne Souaya
*Attorney, Agent, or Firm*—Needle & Rosenberg, P.C.

[57] ABSTRACT

A method of detecting the metastasis of primary breast cancer to a lymph node is provided, comprising detecting, in lymph node tissue, the presence of a nucleic acid of c-myc, PIP or keratin-19. The presence of any one of these nucleic acids in lymph node tissue is associated with metastatic breast cancer. The presence of one or more of these markers in lymph node tissue or other tissue indicates that cells from the primary tumor have migrated from the breast tissue to the lymph node or other tissue. Also provided is a method of predicting the histopathologic stage of a cancer in a patient without having to perform a histopathologic analysis, comprising detecting, in lymph node tissue from the patient, the presence of a nucleic acid of c-myc, the presence of a nucleic acid of c-myc being correlated with stage I cancer as determined by histopathology. Alternatively, the absence of a nucleic acid of PIP and the absence of a nucleic acid of keratin-19 are correlated with stage I cancer as determined by histopathology. In another embodiment, the presence of a nucleic acid of PIP is correlated with stages later than stage I cancer as determined by histopathology. Further, the presence of a nucleic acid of keratin-19 is correlated with stages later than stage I cancer as determined by histopathology. A method of predicting survival time of cancer patients is also provided, comprising detecting, in lymph node tissue from the patient, the presence of a nucleic acid of c-myc, PIP or keratin-19. The presence of a nucleic acid of any of c-myc, PIP or keratin-19 is correlated with a shorter average survival time compared with the presence of none of the nucleic acids.

10 Claims, 3 Drawing Sheets

```
                          SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (xi) SEQUENCE DESCRIPTION: SEQ ID NO:1:

ACGCAGCGCC TCCCTCC                                                    17

(2) INFORMATION FOR SEQ ID NO:2:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (xi) SEQUENCE DESCRIPTION: SEQ ID NO:2:

GGAGGGAGGC GCTGCGT                                                    17

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:3:

GCTCAGGACA ACACTCGGAA                                                 20

(2) INFORMATION FOR SEQ ID NO:4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:4:

ATAACATCAA CGACGGCTGC                                                 20
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:5:

GCGGCGCACC CTTCAGG                                  17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

CCTGAAGGGT GCGCCGC                                  17

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:7:

CTCCTCACAG TGCTTACAG                                19

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

AGTCTCCTTT TCTCCACC                                 18

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

ACAGTAGACA CATATGATGG C                            21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

GTCTACAACC AGCATATCTT C                            21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:11:

TATGCCTATT ATTACAGTGG A                                21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

CCTACTATAA ACCCAGTGAA A                                21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

ATTCTGGCTC AATTATTAGT C                                21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

AAAGAAAAAG CAGGTAAAGT A                                21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

AGACTCTGAG GCTGAGAATA C                                21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

CTGTACTCAT CTTCATAGGC T                                21

(2) INFORMATION FOR SEQ ID NO:17:

```
        (i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:17:

GAGAATGTGA AAATTCCAGT                                                    20

(2) INFORMATION FOR SEQ ID NO:18:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (xi) SEQUENCE DESCRIPTION: SEQ ID NO:18:

CAATCTGCAT ACACCAGTTC                                                    20

(2) INFORMATION FOR SEQ ID NO:19:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (xi) SEQUENCE DESCRIPTION: SEQ ID NO:19:

GCGGCTACAG CTTCACCACC AC                                                 22

(2) INFORMATION FOR SEQ ID NO:20:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (xi) SEQUENCE DESCRIPTION: SEQ ID NO:20:

GGAGGGGCCG GACTCGTCAT A                                                  21
```

MULTI-MARKER RT-PCR PANEL FOR DETECTING METASTATIC BREAST CANCER

BACKGROUND OF THE INVENTION

1. Field of the Invention

The invention relates to the use of multiple markers, detected using RT-PCR to detect metastasis of breast cancer. The invention further relates to the use of multiple markers to determine cancer staging and prognosis.

2. Background Art

Breast cancer remains a leading cause of cancer death among American women [1]. When staging a patient with breast cancer, lymph node status continues to be the most valuable predictor of prognosis. An inverse relationship exists between the number of lymph nodes positive for cancer and the patient's survival [1,2]. The standard method for evaluating the lymph nodes of patients with breast cancer is histologic analysis of hematoxylin and eosin stained sections from axillary lymph nodes within the ipsilateral lymph node basin. Axillary lymph node (ALN) status in breast cancer patients remains the single most important predictor of outcome. However, as many as 30% of patients with pathologically negative lymph nodes ultimately develop recurrent cancer, suggesting that current methods are inadequate for identifying micrometastatic disease [3].

Serial sectioning of these nodes combined with the use of immunohistochemical stains can demonstrate micrometastases in up to 25% of nodes which were "negative" during the routine histopathologic examination process [4,5]. Furthermore, it has been suggested retrospectively that these patients with occult micrometastatic disease have a poorer prognosis [5]. Despite the valuable information it provides, serial sectioning and staining is too cumbersome and costly to be performed as a routine.

Given the significant incidence of missed metastases by routine pathology (and current 30% recurrence rate in node-negative breast cancer patients) a more sensitive method of detecting metastases would be of clear benefit to the clinician making treatment decisions. The present RT-PCR technology applied as a multimarker screening panel is significantly more sensitive and cost-effective method to detect occult axillary lymph node micrometastases in breast cancer patients.

SUMMARY OF THE INVENTION

A novel method of detecting the metastasis of primary breast cancer to a lymph node is provided, comprising detecting, in lymph node tissue, the presence of a nucleic acid associated with breast cancer. The novel method of detecting the metastasis of primary breast cancer to a lymph node can comprise detecting, in lymph node tissue, the presence of a nucleic acid of c-myc, PIP or keratin-19. The presence of any one of these nucleic acids in lymph node tissue is associated with metastatic breast cancer. The presence of one or more of these markers in lymph node tissue or other tissue indicates that cells from the primary tumor have migrated from the breast tissue to the lymph node or other tissue.

Also provided is a method of predicting the histopathologic stage of a cancer in a patient without having to perform a histopathologic analysis. This method is feasible, because the data provided in the Examples correlates the presence of certain markers with certain stages of cancer as determined independently by histopathology. In one embodiment, this method comprises detecting, in lymph node tissue from the patient, the presence of a nucleic acid of c-myc, the presence of a nucleic acid of c-myc being correlated with stage I cancer as determined by histopathology. In a further embodiment, this method comprises determining, in lymph node tissue from the patient, the absence of a nucleic acid of PIP and the absence of a nucleic acid of keratin-19, the absence of nucleic acids of PIP and keratin-19 being correlated with stage I cancer as determined by histopathology. In another embodiment, this method comprises detecting, in lymph node tissue from the patient, the presence of a nucleic acid of PIP, the presence of PIP being correlated with stages later than stage I cancer as determined by histopathology. An additional embodiment of this method comprises detecting, in lymph node tissue from the patient, the presence of a nucleic acid of keratin-19, the presence of keratin-19 being correlated with stages later than stage I cancer as determined by histopathology.

A method of predicting survival time of cancer patients is also provided, comprising detecting, in lymph node tissue from the patient, the presence of a nucleic acid of c-myc, PIP or keratin-19. The presence of a nucleic acid of any of c-myc, PIP or keratin-19 is correlated with a shorter average survival time compared with the presence of none of the nucleic acids. The presence of nucleic acids of two or more of c-myc, PIP or keratin-19 is correlated with a shorter average survival time compared with the presence of only one of the nucleic acids. The presence of nucleic acids of all three of c-myc, PIP and keratin-19 is correlated with a shorter average survival time compared with the presence of only one or two of the nucleic acids.

DETAILED DESCRIPTION OF THE INVENTION

Figure 1:
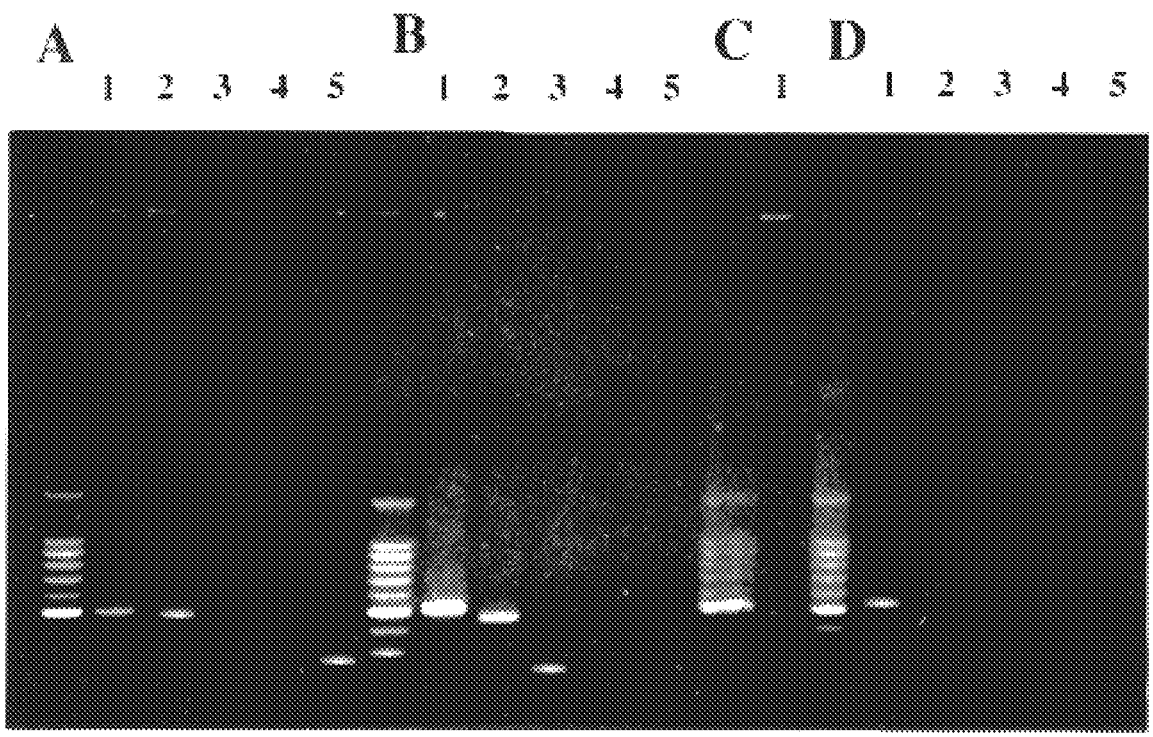
FIGS. 1A, 1B, 1C and 1D show RT-PCR detection of tumor-associated genes in the MB-175 IV breast cancer cell line (FIG. 1A), MDA-MB-231 breast cancer cell line (FIG. 1B), no template negative control (FIG. 1C), and normal cervical lymph node (FIG. 1D). The first lane for each condition is a 100 bp size marker ladder with gene specific primer pairs utilized in the following lanes as follows: 1) β-actin, 2) keratin, 3) c-myc, 4) no primer negative control, 5) PIP. The breast cancer cell line MDA-231 exhibited bands of appropriate size for beta actin, keratin-19, and c-myc; while the cell line MB-175 exhibited β-actin, keratin-19, and PIP. Normal cervical lymph node was only positive for the β-actin internal control.

As used in the specification and in the claims, "a" can mean one or more, depending upon the context in which it is used.

A novel method of detecting the metastasis of primary breast cancer to a lymph node is provided, comprising detecting, in lymph node tissue, the presence of a nucleic acid associated with breast cancer. The novel method of detecting the metastasis of primary breast cancer to a lymph node can comprise detecting, in lymph node tissue, the presence of a nucleic acid of c-myc, PIP or keratin-19. The presence of one or more of these markers in lymph node tissue or other tissue indicates that cells from the primary tumor have migrated from the breast tissue to the lymph node or other tissue. Thus, these nucleic acids are markers for metastasis wherever they are found outside of the primary tumor. Other markers now known or later found to be associated with breast cancer can also be the focus of the present method to detect metastasis.

The nucleic acid being detected is specific for c-myc (Colby et al. (29)), PIP (Shiu et al. (21)) or keratin-19 (Noguchi et al. (14)). Thus, the probes or primers used to detect the nucleic acids can be any nucleic acid that is specific for the particular marker. Alternatively, any nucleic acid that is specific for two or all three of these markers can also be used as the primer of probe in the present method. As used herein to describe a nucleic acid, "specific" means that the nucleotide sequence of the nucleic acid is not found identically in any source other than the stated source. The determination of specificity is made routine, because of the availability of computerized nucleotide sequence databases, wherein an nucleotide sequence of almost any length can be quickly and reliably checked for the existence of identical sequences. If an identical sequence is not found, the nucleic acid is "specific" for the recited source. If the primer or probe used is not specific for c-myc, PIP or keratin-19, a further step of identification must be carried out to establish the presence of one of these markers in the lymph node tissue. Such a step is within the scope of this invention.

The presence of two or more markers in the lymph node or other tissue is more strongly correlated with metastasis than the presence of only one marker. The presence of all three markers is an even stronger indicator that the primary cancer has metastasized. Conversely, if all of the markers are tested for, but none are found, the confidence in the negative findings is stronger than if fewer than all of the markers were tested for.

Also provided is a method of predicting the histopathologic stage of a cancer in a patient without having to perform a histopathologic analysis. This method is feasible, because the data provided in the Examples correlates the presence of certain markers with certain stages of cancer as determined independently by histopathology. In one embodiment, this method comprises detecting, in lymph node tissue from the patient, the presence of a nucleic acid of c-myc, the presence of a nucleic acid of c-myc being correlated with stage I cancer as determined by histopathology. In a further embodiment, this method comprises determining, in lymph node tissue from the patient, the absence of a nucleic acid of PIP and the absence of a nucleic acid of keratin-19, the absence of nucleic acids of PIP and keratin-19 being correlated with stage I cancer as determined by histopathology. In another embodiment, this method comprises detecting, in lymph node tissue from the patient, the presence of a nucleic acid of PIP, the presence of PIP being correlated with stages later than stage I cancer as determined by histopathology. An additional embodiment of this method comprises detecting, in lymph node tissue from the patient, the presence of a nucleic acid of keratin-19, the presence of keratin-19 being correlated with stages later than stage I cancer as determined by histopathology. In still further embodiments, other nucleic acids that are known or later shown to be associated with a particular stage of cancer can be detected in the lymph node or other non-primary breast tissue to predict the cancer stage.

Having provided a means for staging cancer based on the presence of certain markers, the invention allows for more accurate staging of cancers than current techniques allow. In contrast to the standard method of staging breast cancer, which relies on histopathologic detection of cancer in the lymph nodes (in combination with primary tumor size and the presence or absence of cancer elsewhere in the body), the detection of markers as taught in the present invention is more sensitive, and thus, more accurate. As shown herein, the presence of certain of the markers or combinations of markers is indicative of a later stage of cancer than was determined using the standard, histopathology-based methods. The present RT-PCR methodology may provide valuable prognostic information which would allow the clinician to make more informed adjuvant therapy decisions. Thus, the improved information about the stage of a patient's cancer provided by the present methods can be used to tailor a treatment regimen to that patient, increasing the likelihood of improved outcome.

The present method can be used to test paraffin embedded tissues by PCR. These tissues may be from patients currently showing no sign of metastasis according to the usual clinical methods. Thus, testing of the paraffin samples of these patients may be used to inform the doctor and patient of undetected metastasis or the likelihood of later relapse. This method also permits the use of PCR to detect metastasis in specimens that are prepared for the standard histopathologic analysis.

A method of predicting survival time of cancer patients is also provided, comprising detecting, in lymph node tissue from the patient, the presence of a nucleic acid associated with breast cancer. The method of predicting survival time of cancer patients can comprise detecting, in lymph node tissue from the patient, the presence of a nucleic acid of c-myc, PIP or keratin-19. The presence of a nucleic acid of any of c-myc, PIP or keratin-19 is correlated with a shorter average survival time compared with the presence of none of the nucleic acids. The presence of nucleic acids of two or more of c-myc, PIP or keratin-19 is correlated with a shorter average survival time compared with the presence of only one of the nucleic acids. The presence of nucleic acids of all three of c-myc, PIP and keratin-19 is correlated with a shorter average predicted survival time compared with the presence of only one or two of the nucleic acids. It is also noted that, if all of the markers are tested for but none are found, the confidence in the prediction of longer survival time is stronger than if fewer than all of the markers were tested for.

In a method of predicting survival time of cancer patients as provided herein, in one embodiment, this method comprises detecting, in lymph node tissue from the patient, the presence of a nucleic acid of c-myc, the presence of a nucleic acid of c-myc being correlated with longer survival time compared to the presence of PIP or keratin-19. In a further embodiment, this method comprises determining, in lymph node tissue from the patient, the absence of a nucleic acid of PIP and the absence of a nucleic acid of keratin-19, the absence of nucleic acids of PIP and keratin-19 being correlated with longer survival time compared to the presence of these nucleic acids. In another embodiment, this method comprises detecting, in lymph node tissue from the patient, the presence of a nucleic acid of PIP, the presence of PIP being correlated with shorter survival time compared to the presence of c-myc. An additional embodiment of this method comprises detecting, in lymph node tissue from the patient, the presence of a nucleic acid of keratin-19, the presence of keratin-19 being correlated with shorter survival time compared to the presence of c-myc.

In each of the methods described herein, the lymph node tissue can be from the sentinel lymph node. Alternatively, it can be from any of the other lymph nodes. In any of the present methods, lymph node tissue from several or all of the patient's lymph nodes can be tested for the presence or absence of one or more of the described markers.

Furthermore, because the present data show the correlation of the presence of certain markers in non-primary breast tumor tissue with metastasis of the breast cancer, the invention provides a method of detecting metastasis to other tissues. For example, bone marrow (e.g., aspirates), blood, bone and adipose tissue, among others, can be tested for the presence of the markers described herein, as well as for other markers that become associated with breast cancer. Similarly, other nucleic acids that are now known to be associated with breast cancer, or are later found to be associated with breast cancer, can be used in the methods described herein. Examples of these markers are provided below.

There is additional data that supports the use of the present markers to predict disease recurrence. For example, the presence of nucleic acids of one of c-myc, PIP and keratin-19 is correlated with a higher likelihood of recurrence compared with the presence of none of the nucleic acids. The presence of nucleic acids of two or more of c-myc, PIP and keratin-19 is correlated with a higher likelihood of recurrence compared with the presence of only one of the nucleic acids. The presence of nucleic acids of all three of c-myc, PIP and keratin-19 is correlated with a higher likelihood of recurrence compared with the presence of only two of the nucleic acids.

A nucleic acid consisting of the sequence shown in the Sequence Listing as SEQ ID NO:1 is provided. A nucleic acid consisting of the sequence shown in the Sequence Listing as SEQ ID NO:2 is provided. These are specific for the marker c-myc.

A nucleic acid consisting of the sequence shown in the Sequence Listing as SEQ ID NO:3 is also provided. A nucleic acid consisting of the sequence shown in the Sequence Listing as SEQ ID NO:4 is also provided. These are specific for the marker PIP.

A nucleic acid consisting of the sequence shown in the Sequence Listing as SEQ ID NO:5 is also provided. A nucleic acid consisting of the sequence shown in the Sequence Listing as SEQ ID NO:6 is also provided. These are specific for the marker keratin 19.

A nucleic acid consisting of the sequence shown in the Sequence Listing as SEQ ID NO:7 is also provided. A nucleic acid consisting of the sequence shown in the Sequence Listing as SEQ ID NO:8 is also provided. These are specific for the marker MUC1.

A nucleic acid consisting of the sequence shown in the Sequence Listing as SEQ ID NO:9 is also provided. A nucleic acid consisting of the sequence shown in the Sequence Listing as SEQ ID NO:10 is also provided. These are specific for the marker OSN.

A nucleic acid consisting of the sequence shown in the Sequence Listing as SEQ ID NO:11 is also provided. A nucleic acid consisting of the sequence shown in the Sequence Listing as SEQ ID NO:12 is also provided. These are specific for the marker MDR1.

A nucleic acid consisting of the sequence shown in the Sequence Listing as SEQ ID NO:13 is also provided. A nucleic acid consisting of the sequence shown in the Sequence Listing as SEQ ID NO:14 is also provided. These are specific for the marker DCC.

A nucleic acid consisting of the sequence shown in the Sequence Listing as SEQ ID NO:15 is also provided. A nucleic acid consisting of the sequence shown in the Sequence Listing as SEQ ID NO:16 is also provided. These are specific for the marker BNSP.

A nucleic acid consisting of the sequence shown in the Sequence Listing as SEQ ID NO:17 is also provided. A nucleic acid consisting of the sequence shown in the Sequence Listing as SEQ ID NO:18 is also provided. These are specific for the marker HER2.

Blotting techniques can be used for detecting the present marker genes. For example, southern blotting is described herein for detecting markers of metastasis in lymph nodes. The probes used in the southern blots can be the primers described herein that have been labeled to facilitate detection of hybrids. An example of this method is described below.

Although specific examples of primers and probes are provided herein, it is understood that other probes and primers that are specific for a given marker (gene) can be routinely obtained and used in the methods taught herein.

The present invention is more particularly described in the following examples which are intended as illustrative only since numerous modifications and variations therein will be apparent to those skilled in the art.

EXAMPLE 1

Detection of Occult Breast Cancer Micrometastases in Axillary Lymph Nodes

Patients

Sixty one patients undergoing either lumpectomy and axillary dissection or modified radical mastectomy for invasive breast cancer were evaluated. All patients were staged according to AJCC standard criteria by the attending surgeon using relevant clinical data and routine histopathologic analysis of the ipsilateral lymph nodes. Nine patients undergoing carotid endarterectomy without evidence of malignancy were consented for use of their cervical lymph nodes as negative controls.

Axillary Lymph Node Processing

Immediately after resection, the axillary lymph nodes were identified and separated from the specimen by a pathologist. Nodes from levels I, II or III which were greater than 1 cm were bisected, with half of the node sent for routine histologic evaluation and the other half for RT-PCR screening. The cassette used for routine pathologic processing was marked for future identification. The RT-PCR screened lymph nodes were snap frozen in liquid nitrogen immediately to prevent RNA degradation. These were maintained at −70° C. until processed to total RNA was performed. The normal cervical lymph nodes obtained from nine patients undergoing carotid endarterectomy were processed in a similar manner for use as negative controls.

Oligonucleotide Primers

Four specific primer pairs were designed for the following genes: c-myc and PIP (tumor markers expressed in breast cancer specimens), Keratin-19 (an epithelial marker expressed in breast cancer and not in normal lymphatic tissue); and β-actin (used as a positive control, since it is expressed in all tissues). Each gene marker's DNA sequence was identified using the Genbank computer database and Oligo 5.0 software, or based on verification of prior published sequences [8,13,15,23]. The size of each amplified segment was determined using the DNA Strider software so that actual and predicted band size could be compared. The primers were synthesized on an Expedite Nucleic Acid Synthesis System, model 8909 (Perceptive Biosystems). Primer sequences were: 1) c-myc fwd 5' ACGCAGCGC-CTCCCTCC 3' (SEQ ID NO:1), 2) c-myc rev 5' GGAGG-GAGGCGCTGCGT 3' (SEQ ID NO:2), 3) Prolactin inducible protein (PIP) fwd: 5' GCTCAGGACAACACTCGGAA 3' (SEQ ID NO:3), 4) PIP rev: 5' ATAACATCAACGACG-GCTGC 3' (SEQ ID NO:4), 5) Keratin fwd: 5' GCGGCG-CACCCTTCAGG 3' (SEQ ID NO:5)', 6) Keratin rev: 5' CCTGAAGGGTGCGCCGC 3' (SEQ ID NO:6), 7) B-actin fwd: 5' GCGGCTACAGCTTCACCACCAC 3' (SEQ ID NO:19), 8) B-actin rev: 5' GGAGGGGCCGGACTCGT-CATA 3' (SEQ ID NO:20).

Cell Lines

Breast cancer cell lines MDA-MB-231 and MDA-MB-175-VII (ATCC, Rockville, Md.) were maintained in RPMI (Gibco-BRL, Rockville Md.) supplemented with 10% fetal bovine serum at 37° C. in a tissue incubator. Cells were harvested and counted using a standard hemocytometer.

RNA Isolation and RT-PCR

Total cellular RNA was isolated from breast cancer cell lines, normal lymph nodes, and lymph nodes from patients with breast cancer using the guanidium thiocynate-phenol-chloroform method via the RNA-zol protocol (Tel-Test Inc., Friendswood, Tex.). For each lymph node specimen, approximately 1 gram of snap frozen tissue was collected from portions of the harvested lymph nodes and homogenized using a mechanical tissue homogenizer (Biospec Products, Bartlesville, Okla.). Positive control breast cancer cell lines MDA-MB-231 and MDA-MB-175-VII cells were harvested and counted using a hemocytometer with $5\times10^6$ cells used for each RNA isolation. RNA isolation was then performed per protocol and total RNA yield determined by spectrophotometer. Complimentary DNA was made from 5 µg of total RNA using the Superscript II reverse transcriptase kit (GibcoBRL, Gaithersburg, Md.). Briefly, 5 µg of total RNA was combined with oligo (dT) for 10 min at 70° C.; then 10×PCR buffer (4 µl), 25 mM $MgCl_2$ (4 µl), 10 mM dNTP (2 µl), and 0.1 M DTT (4 µl) were added and the sample was incubated for 5 minutes at 42° C. Next, Superscript II Reverse Transcriptase was added (200 units) and the reaction carried out for 50 minutes. Reactions were terminated at 70° C. for 15 minutes and RNase H (2 units) added, and the specimen was incubated for 20 minutes at 37° C. PCR was then performed using 1 µl of cDNA, 1 µl of each gene-specific primer (25 pM), 4 µl 2.5 mM dNTP, 5 µl 10×PCR buffer, 37.8 µl $H_2O$, and 0.2 µl TAQ polymerase. PCR reactions were performed for 25 cycles (94° C.—5 minutes, 30 seconds, 55° C.—30 seconds, 72° C.—7 minutes, 30 seconds) on a thermal cycler (Perkin Elmer Genamp 2400, Foster City, Calif.). The PCR product (10 µl) was loaded into a 1% agarose gel containing ethidium bromide and electrophoresis performed. The gel was examined and photographed using an ultraviolet imager.

Pathologic Analysis

The patients axillary lymph node specimens were processed in standard fashion. This resulted in each patient having two slides per processed block examined by the pathologist after hematoxylin and eosin (H&E) staining. Patient axillary lymph node specimens identified as negative by routine H&E histologic evaluation were then further evaluated. Paraffin blocks containing tissue from lymph nodes were identified and re-sectioned for the additional histologic studies. From 1 to 9 paraffin blocks per patient (a total of 136 blocks) were re-sectioned as follows: the block was faced and consecutive sections were then stained using hematoxylin and eosin, and AE1/AE3 (an immunostain cocktail for identification of cytokeratins, Dako, Carpinteria, Calif.). An additional section served as a negative control for this immunostain. The sequence was repeated after having set aside 15 consecutive sections from the block. This resulted in paired H&E and AE1/AE3 sections taken at two different levels.

The immunocytochemical staining was performed according to standard protocol. Briefly, histologic sections were deparaffinized and hydrated to distilled water. They were then steamed in a vegetable steamer for 20 minutes with Vector Kit antigen unmasking solution (Vector Labs, Burlingame, Calif.), cooled and rinsed with water and 3% hydrogen peroxide. They were then rinsed in PBS×3 for a total of 15 minutes and covered with 10% normal horse serum for 30 minutes. The excess PBS was drained and primary antibody (AE1/AE3) at a dilution of 1:50 was applied for 1 hour at room temperature. The sections were again rinsed in PBS×3 for a total of 15 minutes and then treated with 10% normal horse serum for 10 minutes. After draining the excess PBS, Vector stain biotinylated horse antimouse secondary antisera (Vector Labs, Burlingame, Calif.) was applied for 45 minutes. The sections were again rinsed in PBS×3 and then stained with Vector stain ABC solution for 3 minutes. After a further rinse in PBS×3, Vector diaminobenzedine solution was applied for 10 minutes. Sections were rinsed in distilled water for six rinses and the slides counterstained with Gill's hematoxylin (Lerner Labs, Pittsburgh, Pa.) for 15 seconds. Sections were then dehydrated, cleared and mounted.

A single pathologist reviewed the original routine H&E slides, the recut H&E slides and the immunostained slides in a blinded fashion. Slides which were then positive for micrometastatic disease by either careful review of the original pathology, examination of the additional step section H&E pathology, or examination of the immunostained pathology were noted.

Validation of Multimarker RT-PCR Panel Primers

To establish the validity of a multimarker PCR panel for the detection of occult breast cancer micrometastases in axillary lymph nodes we 1) established the methodology for RT-PCR conditions, 2) demonstrated that the specific primer pairs are able to detect breast cancer cells, and 3) verified that the breast cancer gene specific primer pairs did not amplify genes from normal lymph node tissue. The breast cancer cell line MDA-231 exhibited bands that reflect the presence of β-actin (a ubiquitous gene used as a positive control for the RT-PCR methodology), keratin-19, and c-myc; while the cell line MB-175 exhibited β-actin, keratin-19, and PIP (FIG. 1). These findings demonstrated not only the ability of the RT-PCR panel to detect breast cancer cells, but also validated a multimarker approach as neither cell line expressed all of the screening markers. When RT-PCR was performed using the same methodology on nine control cervical lymph nodes from patients without cancer, each node exhibited the presence of the methodologic control β-actin but no tumor markers, demonstrating the cancer specificity of the screen.

Southern Blot Analysis

Probes for the relevant primers are denatured by heating to 99° C. and then end-labeled by incubation for 60 min. at 37° C. with T45 polynucleotide kinase (promega) and $^{32}$P-ATP. The labeled probes are hybridized to the PCR products by adding 15 μl of the PCR reaction mixtures to 10 μl of a hybridization mixture containing 125 mM EDTA, 150 mM NaCl, a loading dye and one of the probes being utilized. The mixtures are denatured for 5 min. at 95° C., and then annealed at 55° C. The samples are loaded into 10% Tri-borate-EDTA gels (BioRad, Melville, N.Y.) and electrophoresed at 200 V for 45 minutes. The gels are removed from the glass sandwich, wrapped in plastic wrap, placed into a cassette and then autoradiographed on X-Omat AR film (Eastman Kodak Co., Rochester, N.Y.).

Comparison of Multimarker RT-PCR Screening of Breast Cancer Patients Axillary Lymph Nodes to Routine Histopathology For 60 female and one male patient, average age was 55 years, an average of 4.4 (range 1–7) nodes per patient were obtained for RT-PCR analysis as described. The average number of nodes examined in the routine pathologic specimen was 19.6 (range 8–46). The histology for the 61 patients was as follows: 55 with invasive ductal carcinoma, 3 with invasive lobular carcinoma, 1 tubular carcinoma, 1 mucinous carcinoma, and 1 inflammatory carcinoma. Thirty-seven (60%) of these patients were found to have negative lymph nodes by pathologic evaluation. Using the presence of one or more tumor markers (c-myc, keratin-19 or PIP) as criteria for an RT-PCR positive specimen, 15 of the 37 pathologically negative patients exhibited evidence of micrometastases by RT-PCR analysis (40%). Two RT-PCR negatives were found among the 24 histologically positive specimens (8%) (table 1).

TABLE 1

Comparison of Multimarker RT-PCR Screening of Breast Cancer Patients Axillary Lymph Nodes to Routine Histopathology

|  | Pathology positive | Pathology negative | RT-PCR Total |
|---|---|---|---|
| RT-PCR positive | 22 (92%) | 15 (40%) * | 37 (61%) |
| RT-PCR negative | 2 (8%) | 22 (60%) | 24 (39%) |
| Pathology Total | 24 (39%) | 37 (60%) | 61 (100%) |

*two of these pathology negative specimens were positive by step sectioning and immunohistochemical staining.

Comparison of Multimarker RT-PCR Screening to Step Sectioning and Immunohistochemical Staining To be able to compare RT-PCR to the most sensitive methodology available by histopathology, axillary lymph node specimens identified as negative by routine H&E histologic evaluation were then re-evaluated with a blinded review of the original slides and further step sectioning with both H&E and immunohistochemical staining. Remarkably, none of the original slides were found to have missed disease on review. Of the 136 blocks re-cut, only 2 (1 from each of 2 patients) contained deposits of adenocarcinoma previously undiscovered at the time of initial diagnostic examination. These tumor deposits were microscopic and located in the peripheral sinus of the 2 lymph nodes. They were visualized on AE1/AE3 stain and could be located in the adjacent H&E stained sections. However, the deeper sections failed to show the deposits. One of the patients had been RT-PCR positive, and the other was RT-PCR negative. Interestingly, the histology on the latter was a mucinous carcinoma.

Figure 2:
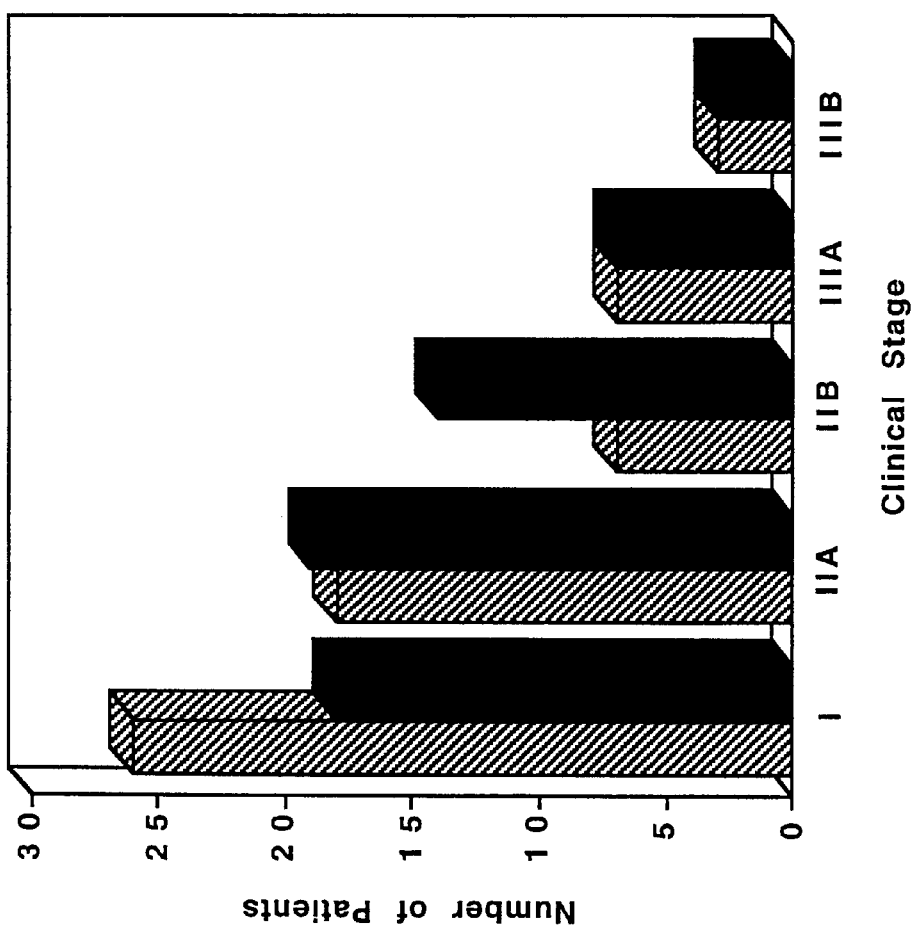
FIG. 2 is a comparison of clinical staging of disease by routine histopathology versus multimarker RT-PCR screening. Diagonal cross-hatching=clinical staging based on routine histopathologic findings. ■=RT-PCR modified clinical staging, with RT-PCR positivity used to define an N1 lymph node.

Staging of Disease by Routine Histopathology Versus Multimarker RT-PCR Screening Using standard criteria and routine histopathology, the AJCC T.M. pathologic stage of this group of patients was: stage I-26, IIA-18, IIB-7, IIIA-7, IIIB-3, and IV-0. RT-PCR positivity in a screened lymph node was then used to define an N1 lymph node status for these patients to better define the potential impact the RT-PCR screen would have on pathologic staging. Using these criteria, RT-PCR identification of micrometastasis upstaged 15 of the 61 patients: stage I-18, IIA-19, IIB-14, III-7, IIIB-3, and IV-0. Eight of 26 pathologically stage I patients (30%) converted to stage IIA, while 7 of 18 stage I.A. patients (39%) were upstaged to IIB (FIG. 2).

Distribution of RT-PCR Markers According to Pathology Staging and Tumor Size

Specific marker frequency was then evaluated. In patients with pathologically positive lymph nodes c-myc was identified in 9 specimens, keratin-19 in 16 and PIP in 7. For pathologically negative patients c-myc was present in 14 specimens, keratin-19 in 2 and PIP in 3. Evaluating all of the RT-PCR panel positive patients, distribution of RT-PCR markers according to pathology staging and tumor size was noted. Interestingly, of the RT-PCR positive individuals who were pathologically stage I, 100% were found to be c-myc positive, 0% keratin and 0% PIP positive. By contrast for the stage IIIB patients only 50% were c-myc positive whereas 100% were positive for both keratin-19 and PIP (table 2). In a similar manner, 100% of the RT-PCR positive patients with T1 lesions were c-myc positive, with 50% keratin-19 and 25% PIP positive. These marker frequencies shifted to 55, 55 and 35% respectively in patients with T2 lesions. The term "T1" is understood to mean tumors of less than of equal to 2 cm, and the term "T2" is understood to mean tumors of less than or equal to 5 cm.

TABLE 2

Distribution of RT-PCR markers according to routine pathology TNM staging and tumor size.

|  | RT-PCR Marker | | |
|---|---|---|---|
| TNM Stage | c-myc | keratin-19 | PIP |
| I | 100% | 0% | 0% |
| II$_A$ | 90% | 40% | 20% |
| II$_B$ | 67% | 67% | 33% |
| III$_A$ | 14% | 57% | 28% |
| III$_B$ | 50% | 100% | 100% |
| T$_1$ | 100% | 50% | 25% |
| T$_2$ + * | 55% | 55% | 35% |

Percentages are derived from the number of individuals expressing a specific marker out of all RT-PCR positive individuals for each particular stage.
*This group includes T2–T4 tumors.

As can be seen, there is a differential distribution of positive RT-PCR markers according to pathology staging and tumor size (table 2). C-myc was present in 100% of stage 1 patients while keratin-19 and PIP were absent. C-myc is a proto-oncogene that plays a role in cell growth, differentiation, and apoptosis. It has been shown to be expressed in in situ cancer as well as invasive cancer, but not necessarily in axillary metastases [15]. It is expressed in 1–15% of all breast cancers and it is associated with high tumor grade and short relapse-free and overall survival [16]. This contrasts with the present data which suggests that c-myc was more commonly present within the earlier stages of breast cancer, and can be identified in axillary lymph nodes. Keratin-19 and PIP were both present with increasing frequency as clinical staging increased. The presence of keratin-19 has been shown to correlate with primary tumor size, lymphovascular invasion, and tumor grade, while PIP has been shown to be present in 61–98% of breast cancer primaries [13,20,23]. PIP was also found to positively correlate to estrogen receptor status, and is therefore thought to be a marker to identify patients with hormonally responsive disease [20]. One study has shown a significant improvement in relapse-free survival in patients who are PIP positive [22]. In contrast, our data would suggest that PIP is present in more advanced disease, and these patients should have a worse prognosis.

Figure 3:
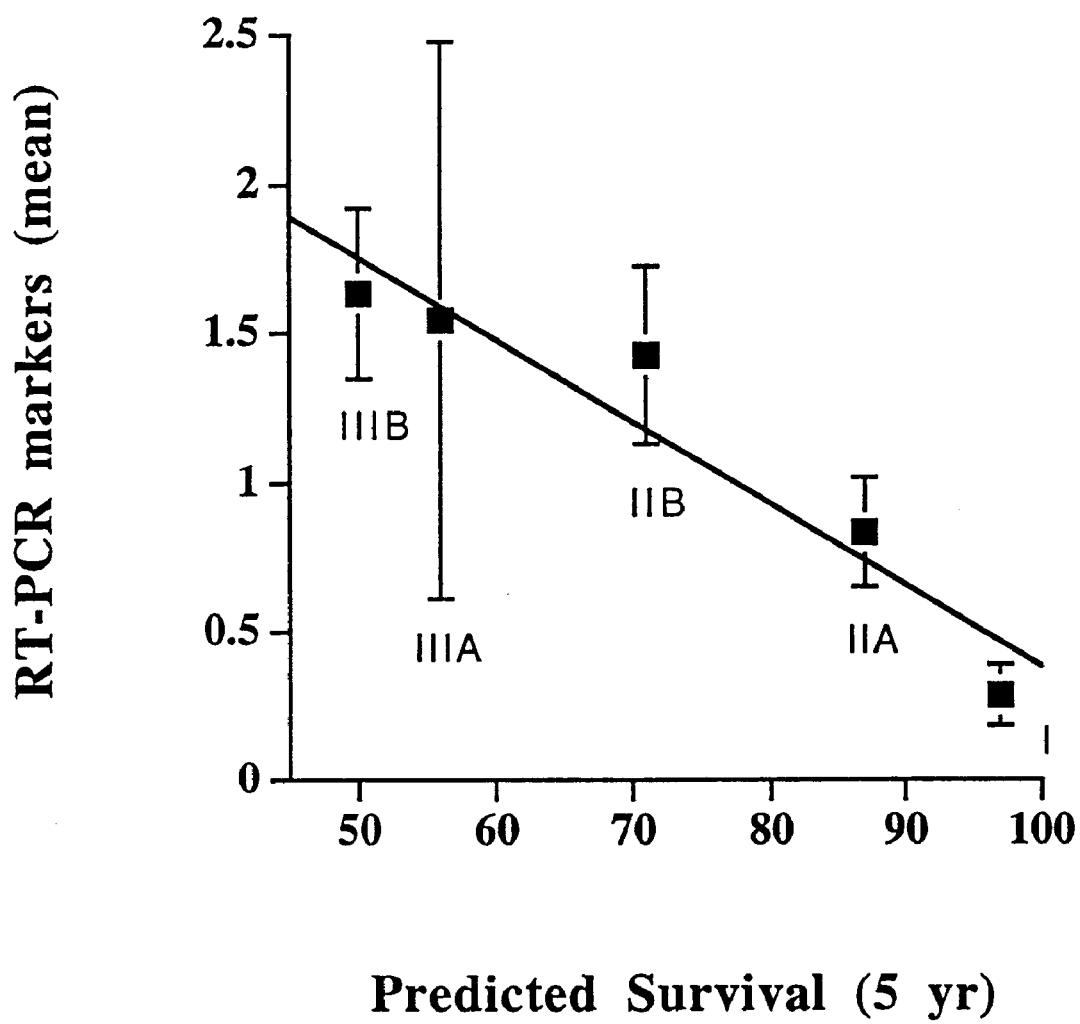
FIG. 3 shows an analysis of the relationship between the number of positive RT-PCR markers and severity of disease based on 5 year predicted survival. The mean number of RT-PCR markers positive per clinical stage upon presentation was calculated using routine histopathology findings to determine N status. Using the AJCC 5 year predicted survival per stage at presentation, a linear regression analysis was performed comparing predicted survival to number of markers positive. The mean number of markers positive is noted on the Y-axis (with standard error and stage of disease noted for each point). The percent survival predicted at five years per stage of disease is plotted along the X-axis. A correlation is noted between the number of positive markers by RT-PCR and predicted survival per stage (r=0.950, p<0.002).

Analysis of the Relationship Between the Number of RT-PCR Markers Positive and Severity of Disease Finally, further analysis was then performed to evaluate whether there was any correlation between the number of positive RT-PCR markers and routine pathologic staging or primary tumor size. Of the 38 specimens found to be positive by RT-PCR, 24 were c-myc positive, 19 keratin-19 positive, and 11 PIP positive. The presence of multiple tumor markers was more common in the histopathologically positive group: 2/24 had 3 markers, 10/24 had two markers, 10/24 had only one marker, and 2/24 only showed the positive control. For the pathologically negative specimens, 1/37 had 3 markers, 2/37 had two markers, 12/37 had one marker, and 22/37 had only the positive control. RT-PCR positivity in this group of patients correlated with primary tumor size with the mean number of RT-PCR markers positive for T1 lesions=0.53±0.148, and for T2 or greater lesions=1.07±0.15 ($p<0.01$). An analysis was then performed to compare the number of markers positive by RT-PCR to predicted survival to evaluate whether increasing number of RT-PCR markers bore any relationship to the severity of disease. The AJCC 5 year predicted survival per stage at presentation based on routine histopathologic evaluation [17] was used for this analysis as the impact of RT-PCR positivity on predicted survival has not currently been established. The mean number of RT-PCR markers positive per clinical stage upon presentation was calculated and a linear regression analysis was performed. A direct correlation appeared to exist between the number of positive markers by RT-PCR and predicted survival per stage ($r=0.950$, $p<0.002$) (FIG. 3).

Summary of Results 37 patients ALN were pathologically negative, of which 15 (40%) were positive by RT-PCR analysis. Two RT-PCR negatives among the 24 histologically positive specimens were detected (8%). The number of patients in each pathologic stage was: I-26, IIA-18, IB.-7, III-7, IIIB-3, and IV-0. By RT-PCR staging, 8 of 26 patients went from I to I.A. (30%), and 7 of 18 from IIA to IIB (39%). Of the RT-PCR positive individuals who were pathologically stage I, 100% were found to be c-myc positive, 0% keratin and 0% PIP positive, whereas for stage IIIB patients these markers were 50%, 100% and 100% respectively. Additionally, an increasing number of positive markers per specimen appeared to correlate with larger primary tumor size ($p<0.01$) and decreased predicted 5 year survival ($r=0.950$, $p<0.002$)).

Conclusions

The present multi-marker RT-PCR based methodology to identify axillary lymph node metastases in patients with breast cancer, appears to be a highly sensitive method for the detection of breast cancer micrometastases. This methodology could help identify patients at high risk for recurrence who may benefit from more aggressive adjuvant therapy, as well as give information about the aggressiveness of each tumor by showing a "footprint" of genetic markers. The sensitivity and low cost of the present RT-PCR staging method provides a powerful complement to routine histopathologic analysis of axillary lymph node biopsies.

EXAMPLE 2

Obtaining and Processing Sentinel Lymph Node and Other Non-Primary Tissue

Sentinel Lymph Node Biopsy

Patients undergo lymphoscintigraphy from 1 to 8 hours prior to the scheduled surgical procedure. Each patient receives approximately 10 mCi of non-filtered 99 technetium sulfur colloid in 4 cc sterile saline. Four 1 cc injections are given circumferentially around but not into either the tumor or biopsy cavity. This is guided either by palpation or ultrasound. Patients whose tumors were diagnosed by radiologic directed biopsy, undergo placement of a Kopans needle using the stereotactic coordinates. After injection of the isotope in the latter patients, the wire is placed, and confirmation of location performed with standard two view mammography. Gamma camera images are then obtained immediately in order to define the pathways of lymphatic drainage and to help identify the approximate location of the sentinel lymph node (SNL).

Patients with palpable tumors or prior open biopsy, undergo intraoperative injection of isosulfan blue dye around the tumor or into the walls of the biopsy cavity. A total of 3–5 cc will be used. Accurate placement of the injection can be facilitated by use of intraoperative ultrasound or by making a small incision down to the area of the lesion but remaining outside the lesion) as directed by the mammogram. Surgical dissection is performed in the usual fashion with tracing the blue lymphatics to the blue lymph node. An intraoperative hand held gamma counter (Neoprobe Corporation, Dublin, Ohio) is used for confirmation of the sentinel node based on 10 second counts. Sentinel node counts should be at least 10×background. The sentinel node is then surgically removed, with background gamma counts evaluated. If still elevated, the area is explored further for the presence of additional sentinel nodes until a negative background is achieved.

In patients undergoing mastectomy, a small axillary incision is made for sentinel node biopsy. The ellipse of skin for the mastectomy is fashioned to incorporate the axillary wound. Once the sentinel node is removed, mastectomy with standard incontinuity axillary dissection can then be performed.

The SLN specimens for standard RT-PCR processing are snap frozen in liquid nitrogen and stored at $-70°$ C. until further processing into RNA.

Bone Marrow Aspirate

The patients left and right anterior superior iliac crests are prepped and draped in the usual fashion. A 10 cc syringe with 18 ga needle is used to aspirate 10 to 12 milliliters of aspirate from two puncture sites on each anterior iliac crest (total of 40–50 ml) and placed in heparinized Falcon tubes with Dulbecco's modified Eagle medium (DMEM, Gibco). The puncture sites are covered with sterile bandages. Bone marrow specimens then undergo isolation of cellular material with density gradient centrifugation, and the cellular component is snap frozen in liquid nitrogen and stored at $-70°$ C. until further processing into RNA.

Peripheral Blood

A total 30–40 cc of blood is drawn from a peripheral vein and stored in appropriate heparinized tubes. Peripheral blood specimens undergo isolation of cellular material with density gradient centrifugation, and the cellular component is snap frozen in liquid nitrogen and stored at −70° C. until further processing into RNA.

Tissue Processing

For SNL testing, approximately 1 gram of snap frozen tissue is collected from portions of each patients harvested SLN and homogenized using a mechanical tissue homogenizer (Biospec Products, Bartlesville, Okla.). Single cell suspensions are washed, counted, and readied for RNA isolation as described in Example 1. The patient's bone marrow aspirate and peripheral blood specimens (processed as described above) are thawed and used for RNA isolation directly as described in Example 1. Briefly, bone marrow aspirate and peripheral blood specimens will be counted using a hemocytometer with $5 \times 10^6$ cells used for each RNA isolation. Total cellular RNA is isolated using the guanidium thiocynate-phenol-chloroform method.

Paraffin Embedded Tissues Processing

Five 4 μm sections from each block of a patients paraffin-embedded blocks will be cut onto glass slides, dewaxed in xylene, and rehydrated. The RNA from these tissue sections will then be extracted by incubating in extraction buffer (100 mmol/l NaCl, 10 mmol/l Tris-HCl, 25 mmol/l EDTA, and 0.5% wt/vol SDS) containing 2 mg/ml proteinase K, at 37° C. for 3 days. RNA will then be extracted using 300 μl of phenol (ph 4.5–5.5) and chloroform (1;1). The top RNA containing layer will be removed and used for subsequent RT-PCR analysis as previously described.

cDNA Processing an RT-PCR

This methodology is essentially the same as the axillary lymph node protocol described in Example 1 for all of the aforementioned specimens.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Henderson I, Harris J, Kinne D, Hellman S. Cancer of the Breast. In: Cancer, Principles and Practice of Oncology, ed. DeVita V, Hellman S, Rosenberg S, 3rd ed. Philadelphia: J B Lippincott; 1989: 1197–1268.
2. Valaguusa P, Bonadonna G, Veronesi U. Patterns of relapse and survival following radical mastectomy. Cancer 1978; 41: 1170–1178.
3. Gardner B, Feldman J. Are positive axillary nodes in breast cancer markers for incurable disease? Ann Surg 1993; 218: 270–277.
4. Bettelheim R, Price K, Goldhirsch A. Prognostic importance of occult axillary lymph node micrometastases from breast cancer. Lancet 1990; 335: 1565–1568.
5. McGurkin M, Cummings M, Walsh M, et al. Occult axillary node metastases in breast cancer: their detection and prognostic significance. Br J Cancer 1996; 73:88–95.
6. Mori M, Mimor K, Inove H, et al. Detection of cancer micrometastases in lymph nodes by reverse transcriptase polymerase chain reaction. Cancer Res 1995; 55:3417–3420.
7. Noguchi S, Aihara R, Nakamor S, et al. The detection of breast carcinoma micrometastases in axillary lymph nodes by means of reverse-transcriptase polymerase chain reaction. Cancer 1994; 74: 1595–1600.
8. Noguchi S, Aihara R, Nakamor S, et al. The detection of breast carcinoma micrometastases in axillary lymph nodes by means of reverse-transcriptase Polymerase chain reaction. Comparison between muc1 mRNA and keratin-19 mRNA amplification. Am J Path 1996; 148: 649–656.
9. Traweek S, Liu T, Battifora H. Keratin gene expression in non-epithelial tissues. Detection with polymerase chain reaction. Am J Path 1993; 142:1111–1117.
10. Wu S, Ben-Ezra J, Colombero A. Detection of micrometastases in breast cancer by the polymerase chain reaction: a feasibility study. Lab Invest 1990; 62: 109A.
11. Datta Y, Adams P, Drobyski W, et al. Sensitive detection of occult breast cancer by the reverse-transcriptase polymerase chain reaction. J Clin Immunol 1994;12: 475–482.
12. Schoenfeld A, Luqmani Y, Smith D, et al. Detection of breast cancer micrometastases in axillary lymph nodes by using polymerase chain reaction. Cancer Res 1994; 54: 2986–2990.
13. Schoenfeld A, Luqmani Y, Sinnett H D, et al. Keratin 19 mRNA Measurement to detect micrometastases in lymph nodes in breast cancer patients. Br J Cancer 1996; 74: 1639–1642.
14. Noguchi S, Aihara R, Motamura K, et al. Histologic characteristics of breast cancers with occult lymph node metastases detected by keratin 19 mRNA reverse transcriptase-polymerase chain reaction. Cancer 1996; 78: 1235–1240.
15. Watson P, Safneck J, Le K, et al. Relationship of c-myc amplification to progression of breast cancer from in situ to invasive tumor and lymph node metastasis. JNCI 1993; 85: 902–907.
16. Watson P, Singh R, Hole A. Influence of c-myc on the progression of human breast cancer. Curr Topics Micro Immunol 1996; 213: 267–283.
17. Berns E, Foekens J, van Staveren I, et al. Oncogene amplification and prognosis in breast cancer: relationship with systemic treatment. Gene 1995; 159: 11–18.
18. Berns E, Klijn J, VanPutten W, et al. C-myc amplification is a better prognostic factor than her2/neu amplification in primary breast cancer. Cancer Res 1992; 52: 1107–1113.
19. Castro A, Buschbaum P, Nadji M, et al. Tissue immunoreactive prolactin hormone in breast cancer. Res Comm Chem Path Pharm; 1990, 29: 159–170.
20. Murphy L, Lee-Wing M, Goldenberg G, Shiu R. Expression of the gene encoding a prolactin-inducible protein by human breast cancers in vivo: correlation with steroid receptor status. Cancer Res 1987; 47: 4160–4164.
21. Shiu R, Iwasiow B. Prolactin-inducible proteins in human breast cancer cells. J Biol Chem 1985; 260: 11307–11313.
22. Pagani A, Sapino A, Eusebi V, et al. PIP/GCDFP-15 Gene expression and apocrine differentiation in carcinomas of the breast. Virchows Archive 1994; 425: 459–465.
23. Clark J, Shiu R, Orr F, Watson P. Reverse transcription polymerase chain reaction assay for prolactin-inducible protein gene expression to detect human breast cancer micrometastasis. PNAS, 1996; 37:86–87.
24. Hoon D, Wang Y, Dale P, et al. Detection of occult melanoma cells in blood with a multiple-marker polymerase chain reaction assay. J Clin Onc 1995; 13: 2109–2116.
25. Data on file with the National Cancer Data Base (Commission on Cancer of the American College of Surgeons and the American Cancer Society), 1989.
26. Myal Y, Robinson D, Iwasiow B, Tsuyuki D, Wong P, and Shiu R. The prolactin-inducible protein (PIP/GCDFP-15) gene: cloning, structure and regulation. Endocrinology 1991; 80:165–175.

27. Wreschener D, Hareuveni M, Tsarfaty I, Smorodinsky N, Horov J, Zaretsky J, Kotkes P, Weiss M, Lathe R, Dion A, and Keydar I. Human epithelial tumor antigen cDNA sequences. Differential splicing may generate multiple protein forms. Eur. J. Biochem. 1990; 189:463–473.
28. Hijya N, Setoguchi M, Matsuura K, Higuchi Y, Akizuki S, and Yamamato S. Cloning and characterization of the human osteopontin gene and its promoter. Biochem. J. 1994; 303:255–262.
29. Colby W, Chen E, Smith D, and Levinson D. Identification and nucleotide sequence of a human locus homologus to the v-myc oncogene of avian myelocytomatosis virus MC29. Nature 1983; 301:722–725.
30. Madden M, Morrow C, Nakagawa M, Goldsmith M, Fairchild C and Cowan K. Identification of 5' and 3' sequences involved in the regulation of tanscription of the human mdr 1 gene in vivo. The J. of Biol. Chem. 1993; 268:8290–8297.
31. Hedrick L, Kathleen R, Fearon E, Wu T, Kinzler K and Vogelstein B. The DCC gene product in cellular differentiation and colorectal tumorigenesis. Genes and Develop. 1994; 8:1174–1183.
32. Kim R, Shapiro H, Li J, Wrana J, and Sodek J. Characterization of the human bone sialo protein (BSP) gene and its promoter sequence. Matrix Biology 1994; 14:31–40.
33. Coussens L, Yang-Feng T, Liao Y, Chen E, Gray A, McGrath J, Seeburg P, Libermann T, Schlessinger J, Francke U, Levinson A and Ullrich A. Tyrosine kinase receptor with extensive homology to EGF receptor shares chromosomal location with neu oncogene. Science 1985; 230:1132–1139.

What is claimed is:

1. A method of detecting the metastasis of primary breast cancer to a lymph node, comprising detecting, in lymph node tissue, the presence of a nucleic acid of c-myc, PIP, a combination of c-myc and keratin-19, a combination of c-myc and PIP, a combination of c-myc, keratin-19 and PIP or a combination of PIP and keratin-19, the presence of any of these nucleic acids or combinations of nucleic acids in lymph node tissue being associated with metastatic cancer.

2. The method of claim 1, wherein the lymph node tissue is from the sentinel lymph node.

3. A method of determining the lower likelihood of survival to five years of a cancer patient, comprising detecting, in lymph node tissue from the patient, the presence of the nucleic acids of two or more of c-myc, PIP or keratin-19, the presence of two or more of c-myc, PIP or keratin-19, being correlated with a lower likelihood of survival to five years compared to the likelihood of survival to five years of a cancer patient having only c-myc in lymph node tissue.

4. The method of claim 3, wherein the lymph node tissue is from the sentinel lymph node.

5. A method of identifying a cancer patient as likely to have stage I cancer as determined by AJCC staging criteria, comprising detecting, in lymph node tissue from the patient, the absence of a nucleic acid of PIP, the absence of a nucleic acid of keratin-19 and the presence of a nucleic acid of c-myc, the absence of a nucleic acid of PIP, the absence of a nucleic acid of keratin-19 and the presence of a nucleic acid of c-myc being correlated with stage I cancer as determined by AJCC staging criteria.

6. The method of claim 5, wherein the lymph node tissue is from the sentinel lymph node.

7. A method of identifying a cancer patient as likely to have a stage of cancer later than stage I as determined by AJCC staging criteria, comprising detecting, in lymph node tissue from the patient, the presence of a nucleic acid of PIP, the presence of a nucleic acid of PIP being correlated with stages later than stage I cancer as determined by AJCC criteria.

8. The method of claim 7, wherein the lymph node tissue is from the sentinel lymph node.

9. A method of identifying a cancer patient as likely to have a stage of cancer later than stage I as determined by AJCC criteria, comprising detecting, in lymph node tissue from the patient, the presence of a nucleic acid of keratin-19, the presence of a nucleic acid of keratin-19 being correlated with stages later than stage I cancer as determined by AJCC criteria.

10. The method of claim 9, wherein the lymph node tissue is from the sentinel lymph node.

* * * * *